«12» United States Patent [19]
Holton

[11] Patent Number: 6,080,920
[45] Date of Patent: Jun. 27, 2000

[54] TRANSGENIC PLANTS EXHIBITING ALTERED FLOWER COLOR AND METHODS FOR PRODUCING SAME

[75] Inventor: Timothy Albert Holton, Northcote, Australia

[73] Assignee: International Flower Developments Pty. Ltd., Victoria, Australia

[21] Appl. No.: 08/809,928

[22] PCT Filed: May 16, 1996

[86] PCT No.: PCT/AU96/00296

§ 371 Date: Jun. 12, 1997

§ 102(e) Date: Jun. 12, 1997

[87] PCT Pub. No.: WO96/36716

PCT Pub. Date: Nov. 21, 1996

[30] Foreign Application Priority Data

May 16, 1995 [AU] Australia ............................ PN2988/95

[51] Int. Cl.⁷ .............................. A01H 5/00; C12N 15/82
[52] U.S. Cl. ...................... 800/323.3; 800/282; 800/298; 800/323; 800/323.2
[58] Field of Search .................................. 800/205, 282, 800/298, 323, 323.2, 323.3

[56] References Cited

U.S. PATENT DOCUMENTS 5,410,096   4/1995   Meyer et al. ......................... 800/323.1

FOREIGN PATENT DOCUMENTS

WO 93/18155   11/1992   WIPO .

OTHER PUBLICATIONS

Webster's II Dictionary, p. 596, 1994.
Meyer et al. A new petunia flower colour generated by transformation of a mutant with a maize gene. Nature. 330(6149):677–678, Dec. 1987.
Holton, T.A. Modification of flower colour via manipulation of P450 gene expression in transgenic plants. Drug Metabolism and Drug Interactions. 12(3–4):359–368, 1995.
J.S.N. Oud et al. (1995)"Breeding of Transgenic orange Petunia hybrida varieties" *Euphitica* 84(3): 175–181.
P. Elomaa et al. (1994) "Modification of Flower Colour using Genetic Engineering" *Biotechnol. Genet. Eng. Rev.* 12: 79–81.
K. Stich et al. (1992) "Enzymatic conversion of dihydroflavonols to flavan–3,4–diols using flower extract of *Dianthus caryophyllus* L. (carnation)" *Planta* 187(1): 103–108.
G. Forkmann et al., (1987) "Distinct Substrate Specificity of Dihydroflavanol–4–Reductase from Flowers of *Petunia hybrida*" *Z. Naturforsch, C: Biosci.* 42: 1146–1148.

*Primary Examiner*—Amy Nelson
*Attorney, Agent, or Firm*—Scully, Scott, Murphy & Presser

[57] ABSTRACT

The present invention relates generally to novel approaches in generating transgenic plants exhibiting altered flower colour by the introduction of a nucleotide sequence encoding dihydroflavonol-4-reductase (DFR) which preferably acts on dihydromyricetin (DHM). More particularly, the present invention provides transgenic carnation plants and flowers cut therefrom exhibiting flower colouration not naturally associated with carnation plants. The present invention further contemplates methods for producing transgenic carnation plants with the altered flower colour.

21 Claims, 7 Drawing Sheets

TRANSGENIC PLANTS EXHIBITING ALTERED FLOWER COLOR AND METHODS FOR PRODUCING SAME

The present invention relates generally to novel approaches in generating transgenic plants exhibiting altered flower colour. More particularly, the present invention provides transgenic carnation plants and flowers cut therefrom exhibiting flower colouration not naturally associated with carnation plants. The present invention further contemplates methods for producing transgenic carnation plants with the altered flower colour.

Bibliographic details of the publications referred to in this specification are collected at the end of the description. Sequence Identity Numbers (SEQ ID NOs.) for the nucleotide sequences referred to in the specification are defined following the bibliography.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

BACKGROUND OF THE INVENTION

The rapidly increasing sophistication of recombinant DNA technology is greatly facilitating a broad spectrum of industrial processes from the horticultural to medical and allied health industries. The horticultural and related agricultural industries are particularly benefiting from that advances in recombinant DNA technology.

The floriculture industry in particular strives to develop new and different varieties of flowering plants, with improved characteristics ranging from disease and pathogen resistance to altered flower colour. Although classical breeding techniques have been used with some success, this approach has been limited by the constraints of a particular species' gene pool. It is rare, for example, for a single species to have a full spectrum of coloured varieties. Accordingly, substantial effort has been directed towards the use of recombinant DNA technology to generate transgenic plants exhibiting the desired characteristics.

The development of varieties of the major cutflower species such as carnation plants, for example, having flowers exhibiting a range of colours covering lilac, violet, purple and blue or various shades thereof, would offer a significant opportunity in both the cutflower and ornamental markets.

Flower colour is predominantly due to two types of pigment: flavonoids and carotenoids. Flavonoids contribute to a range of colours from yellow to red to blue. Carotenoids impart an orange or yellow tinge and are commonly the only pigment in yellow or orange flowers. The flavonoid molecules which make the major contribution to flow colour are the anthocyanins which are glycosylated derivatives or cyanidin, delphinidin, petunidin, peonidin, malvidin and pelargonidin, and are localised in the vacuole. The different anthocyanins can produce marked differences in colour. Flower colour is also influenced by co-pigmentation with colourless flavonoids, metal complexation, glycosylation, acylation, methylation and vacuolar pH (Forkmann, 1991).

The biosynthetic pathway for the flavonoid pigments (hereinafter referred to as the "flavonoid pathway") is well established (Ebel and Hahlbrock, 1988; Hahlbrock and Grisebach, 1979; Wiering and de Vlaming, 1984; Schram et al., 1984; Stafford, 1990). The first committed step in the pathway involves the condensation of three molecules of malonyl-CoA with one molecule of p-coumaroyl-CoA. This reaction is catalysed by the enzyme chalcone synthase (CHS). The product of this reaction, 2',4,4',6'-tetrahydroxychalcone, is normally rapidly isomerized to produce naringenin by the enzyme chalcone-flavanone isomerase (CHI). Naringenin is subsequently hydroxylated at the 3-position of the central ring by flavanone 3-hydroxylase (F3H) to produce dihydrokaempferol (DHK).

Figure 1:
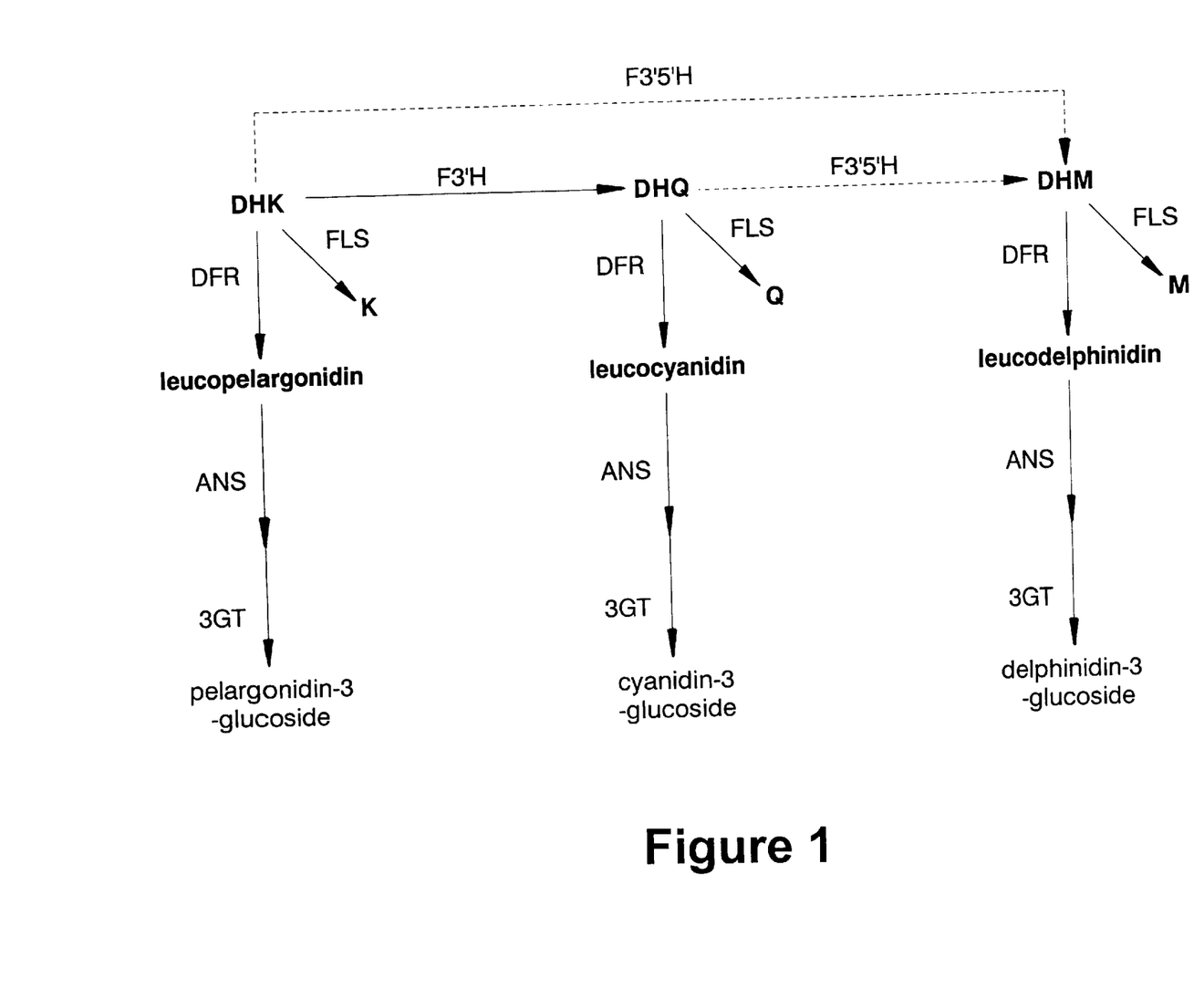
FIG. 1 is a schematic diagram of the pathways for conversion of dihydroflavonols to flavonols and anthocyanins. Abbreviations: DHK=dihydrokaempferol, DHQ=dihydroquercetin, DHM=dihydromyricetin, K=kaempferol, Q=quercetin, M=myricetin, F3'H=flavonoid 3'-hydroxylase, F3'5'H=flavonoid 3',5'-hydroxylase, FLS=flavonol synthase, DFR=dihydroflavonol-4-reductase, ANS=anthocyanidin synthase, 3GT=flavonoid 3-glucosyltransferase.

The B-ring of dihydrokaempferol (DHK) can be hydroxylated at either the 3', or both the 3' and 5' positions, to produce dihydroquercetin (DHQ) and dihydromyricetin (DHM), respectively (see FIG. 1). DHQ is an intermediate required for the production of cyanidin-based anthocyanins and DHM is an intermediate required for the production of delphinidin-based anthocyanins in the flavonoid pathway. Two key enzymes involved in this pathway are flavonoid 3'-hydroxylase (F3'H) and flavonoid 3',5'-hydroxylase (F3'5'H). The F3'H acts on DHK to produce DHQ. The F3'5'H is a broad spectrum enzyme catalyzing hydroxylation of DHK in the 3' and 5' positions and of DHQ in the 5' position (Stotz and Forkmann, 1982), in both instances producing DHM. The pattern of hydroxylation of the B-ring of anthocyanins plays a key role in determining petal colour.

Another key enzyme is dihydroflavonol-4-reductase (DFR) which has variable substrate specificity depending on its plant source and has the potential to act on any one or more of DHK, DHQ and DHM.

Many of the major cutflower species lack the F3'5'H and consequently cannot display the range of colours, resultant from synthesis of delphinidins and derivatives thereof, that would otherwise be possible. This is particularly the case for carnations which constitute a major proportion of the worldwide cutflower market. There is a need, therefore, to modify carnation plants to generate transgenic plants which are capable of producing the F3'5'H, thereby providing a means of converting DHK and DHQ to DHM, thereby influencing the hydroxylation pattern of the anthocyanins and allowing the production of anthocyanins derived from delphinidin. Flower colour is modified as a result and a single species is able to express a broader spectrum of flower colours.

SUMMARY OF THE INVENTION

In work leading up to the present invention, the inventors sought to genetically manipulate the flavonoid pathway in carnation plants to generate a range of plants with the capacity to direct DHK metabolism towards delphinidin in preference to or rather than pelargonidin or cyanidin. The resulting plants exhibit altered flower colouration relative to presently available carnation plants. The new transgenic carnation plants and more particularly flowers cut therefrom fulfill a long-felt need in the horticultural and more particularly the floricultural industry in relation to carnations. The technology of the present invention is also applicable to a range of other flowering plants such as roses and chrysanthemums.

Accordingly, one aspect of the present invention contemplates a method for producing a plant exhibiting altered flow colour, said method comprising selecting a plant which is substantially incapable of synthesizing a DFR which acts on DHK and introducing into said selected plant one or more genetic constructs comprising nucleotide sequences encoding a F3'5'H and a DFR which is capable of acting on DHM but substantially incapable of acting on DHK.

Accordingly, one aspect of the present invention contemplates a method for producing a plant exhibiting altered flower colour, said method comprising selecting a plant from which said first plant is to be derived wherein said selected plant is substantially incapable of synthesizing a DFR which acts on DHK and introducing into said selected plant one or more genetic constructs comprising nucleotide sequences encoding a F3'5'H and a DFR which is capable of acting on DHM but substantially incapable of acting on DHK.

More particularly, the present invention provides a method for producing a carnation plant exhibiting altered flower colour, said method comprising selecting a carnation plant from which said first carnation plant is to be derived wherein said selected plant is substantially incapable of synthesizing a DFR which acts on DHK in flowers and introducing into said selected plant one ore more genetic constructs comprising nucleotide sequences encoding a F3'5'H and a DFR which is capable of acting on DHM but substantially incapable of acting on DHK.

The present invention is exemplified herein using carnation plants. This is done, however, with the understanding that the instant invention extends to a range of flowering plants such as but not limited to roses and chrysanthemums. Reference hereinafter to carnations should be taken as reference to other suitable flowering plants.

Another aspect of the present invention is directed to a method for producing a carnation plant exhibiting altered flower colour, said method comprising the steps of:

(i) selecting a plant from which said carnation plant is to be derived wherein said selected plant is substantially incapable of synthesizing a DFR which acts on DHK in flowers;

(ii) transforming cells of said selected plant with one or more genetic constructs comprising nucleotide sequences which encode separately F3'5'H and DFR provided said DFR is capable of acting on DHM but substantially incapable of acting on DHK;

(iii) regenerating a transgenic plant from said transformed cells such that said regenerated plant is capable of expressing said F3'5'H and said DFR of step (ii); and (iv) growing said plant under conditions to permit expression of said F3'5'H and said DFR of step (ii) in flowers.

Reference herein to altered flower colour includes alteration in the colour of any or all components of the flower including the petal, sepal and stamen. Conveniently, altered flower colour is shown by comparing the flower colour of a transgenic plant made in accordance with the present invention with a plant of the same species but which possesses a DFR which can act on DHK. In practical terms, a comparison may be made between the transgenic plant and the "selected" plant, i.e. the plant from which the transgenic plant is derived.

The present invention is predicated in part of the genetic manipulation of the anthocyanin pathway in carnation plants to direct metabolism of DHK preferentially towards DHM and delphinidin and derivatives thereof rather than through leucopelargonidin and pelargonidin derivatives or DHQ and leucocyanidin and cyanidin derivatives. Flowers of carnation plants lack a F3'5'H and, hence, DHK is unable to undergo metabolism down the delphinidin pathway which is required in order to produce flower colours in the range covering lilac, violet, purple and blue or various shades thereof. To achieve a preferential re-direction of DHK metabolic products down the delphinidin pathway, the inventors screened for and located white lines of carnations lacking a functional DFR. Expression of an introduced nucleic acid molecule results in a F3'5'H which is capable of directing DHK metabolism to DHM. Introduction and expression of a nucleic acid molecule encoding a non-indigenous DFR which is capable of acting on DHM but not DHK, then results in DHM metabolism being directed to leucodelphinidin thereby allowing subsequent conversion to other derivatives of delphinidin. Little or no metabolism occurs via the pelargonidin or cyanidin pathway.

In a particularly preferred embodiment, the flowers of the starting plant also lack a F3'H.

According to this preferred embodiment, the present invention contemplates a method for producing a carnation plant exhibiting altered flower colour properties, said method comprising selecting a carnation plant from which said first mentioned carnation plant is to be derived wherein said selected plant is substantially incapable of synthesizing either a F3'H or a DFR which can act on DHK in flowers and introducing into said selected plant one or more genetic constructs comprising nucleotide sequences encoding an F3'5'H and a DFR which is capable of acting on DHM but substantially incapable of acting on DHK.

More particularly, this aspect of the present invention is directed to a method for producing a carnation plant exhibiting altered flower colour, said method comprising the steps of:

(i) selecting a carnation plant from which said first mentioned carnation plant is to be derived, wherein said selected plant is substantially incapable of synthesizing either F3'H or a DFR which can act on DHK in flowers;

(ii) transforming cells of said selected plant which one or more genetic constructs comprising nucleotide sequences which encode separately F3'5'H and DFR provided said DFR is capable of acting on DHM but substantially incapable of acting on DHK;

(iii) regenerating a transgenic plant from said transformed cells such that said regenerated plant is capable of expressing said F3'5'H and said DFR of step (ii); and (iv) growing said plant under conditions to permit expression of said F3'5'H and said DFR of step (i) in flowers.

The present invention is exemplified herein using petunia DFR as an enzyme capable of acting on DHM but not DHK. This is done, however, with the understanding that the present invention extends to a DFR enzyme from any plant providing it is capable of acting on DHM but not DHK. Similarly, a particularly useful F3'5'H is from petunia but other sources of F3'5'H include egg plant, lisianthus, gentian, pansy, china aster, anemone, grape, iris, hyacinth, delphinium and bell flower.

Reference herein to the ability of a plant to produce or not produce an enzyme such as DFR, F3'H and F3'5'H relates to its ability in flowers and not necessarily elsewhere in the plant.

A particularly preferred embodiment of the present invention relates to a method for producing a carnation plant exhibiting altered flower colour, said method comprising selecting a carnation plant from which said first carnation plant is to be derived wherein said selected plant is substantially incapable of synthesizing either F3'H or a DFR which can act on DHK in flowers, introducing into cells of said selected plant one or more genetic constructs comprising nucleotide sequences which separately encode a F3'5'H and a petunia DFR, regenerating a plant from said cells, and then growing said plant under conditions sufficient to permit expression of said F3'5'H and said petunia DFR such that said plant produces flowers of different colour relative to said selected plant. Preferably, the F3'5'H is of petunia origin.

The selected plant from which the subject transgenic plant exhibiting altered flower colour is derived may be a natural mutant for DFR such that it substantially does not produce DFR or produces reduced levels of this enzyme, or produces the enzyme with altered substrate specificities such as substantial inability to metabolize DHK. Preferably, however, the selected plant is a double mutant for DFR and F3'H. Mutants of these types wold generally have white flowers. Mutations may be single or multiple nucleotide substitutions, deletions and/or additions to the nucleotide sequences defining the enzymes. Alternatively, the mutations may be induced or directed by, for example, transposon tagging, oligonucleotide-directed mutagenesis, Agrobacterium-directed mutagenesis or viral-directed mutagenesis.

Alternatively, genetic constructs may be introduced to reduce expression of DFR and/or F3'H by, for example, antisense or co-suppression methods. In this aspect of the invention, a plant may be chosen with substantial inability to synthesize one of DFR or F3'H and a genetic sequence introduced to reduce expression of the other of said DFR or F3'H. Alternatively, a plant may be selected with substantial inability to synthesise one of DFR or F3'H and a mutation induced in the other of said DFR or F3'H, by any of the means mentioned above. In either case, the resulting plant would be a "selected" plant and a recipient for a F3'5'H and a DFR capable of acting on DHM but not DHK. A "selected" plant may also be considered a "parent" plant since it is from this plant that a transgenic plant exhibiting altered flower colour is derived in accordance with the methods of the present invention.

The altered flower colour contemplated by the present invention includes the ability of the carnations to produce a range of colours including lilac, violet, purple and blue flowers or various shades thereof from, for example, deep mauve to dark blue to a violet colour or their various shades or combinations thereof.

Another aspect of the present invention contemplates a transgenic plant exhibiting altered flower colour, said plant being substantially incapable of synthesizing a DFR which acts on DHK and which carries a nucleic acid molecule comprising a sequence of nucleotides which encodes a F3'5'H and a DFR which is capable of acting on DHM but substantially incapable of acting on DHK.

Preferably, the plant is a carnation, rose, gerbera or chrysanthemum. In accordance with this aspect of the present invention, the nucleic acid molecule may comprise multiple genetic constructs separately encoding DFR and F3'5'H or a single combined genetic construct encoding both enzymes but with expression being generally directed by two separate promoters. The term "nucleic acid molecule" encompasses single or multiple nucleic acid molecules.

In a preferred aspect of the present invention, there is provided a carnation plant exhibiting the following properties:

(i) a substantial inability to synthesize a DFR which acts on DHK;

(ii) an ability to synthesize a non-indigenous DFR which is capable of acting on DHM but is substantially incapable of acting on DHK; and (iii) an altered flower colour relative to a carnation plant which expresses a DFR which acts on DHK.

Preferably, the carnation plant is also substantially incapable of synthesizing a F3'H. According to this preferred embodiment, there is provided a carnation plant exhibiting the following properties:

(i) a substantial inability to synthesize a F3'H;

(ii) a substantial inability to synthesize a DFR which acts on DHK;

(iii) an ability to synthesize a non-indigenous DFR which is capable of acting on DHM but is substantially incapable of acting on DHK; and (iv) an altered flower colour relative to a carnation plant which expresses a F3'H and/or a DFR which acts on DHK.

The present invention extends to the flowers and in particular flowers cut from such transgenic carnations or from plants produced according to the methods herein disclosed.

A "non-indigenous" DFR is an enzyme not normally produced in carnation plants and, in one preferred embodiment, is from petunia. A "non-indigenous" DFR may alternatively have originated from a carnation plant but has undergone mutation to restrict its substrate specificity to DHM. The F3'5'H is also non-indigenous and in one aspect is preferably from petunia.

Another aspect of the present invention contemplates a method for producing carnation flowers exhibiting altered flower colour, said method comprising growing a transgenic flowering carnation plant for a time and under conditions for flowers to form and then optionally harvesting said flowers, said transgenic carnation plant having been genetically manipulated such that:

(i) it is substantially incapable of expressing a DFR which is capable of acting on DHK;

(ii) it is capable of expressing a non-indigenous F3'5'H; and (iii) it is capable of expressing a non-indigenous DFR which is capable of acting on DHM but is substantially incapable of acting on DHK.

In accordance with this aspect of the present invention, the flowers exhibiting altered flower colour will now have the capacity to metabolise DHK to DHM and delphinidin and derivatives thereof of the flavonoid pathway.

Preferably, the transgenic plant is also substantially incapable of expressing a F3'H.

Other aspects of the present invention include the use of genetic sequences encoding separately a F3'5'H, a DFR which is capable of acting on DHM but is substantially incapable of acting on DHK, and optionally also a F3'H, in the genetic manipulation of a carnation plant substantially incapable of expressing or synthesizing an active DFR capable of acting on DHK or DHM, so as to allow the manufacture of a carnation plant exhibiting altered flower colour compared to a carnation plant which is capable of synthesizing a DFR capable of acting on DHK. In a related aspect, the present invention extends to flowers and in particular flowers cut from said carnation plants.

The present invention is further described by reference to the following figures and/or examples.

BRIEF DESCRIPTION OF THE DRAWINGS

FIG. 3 is a diagrammatic representation of the binary expression vector pCGP1470, construction of which is described in Example 9. Tc resistance=the tetracycline resistance gene; LB=left border; RB=right border; surB=the coding region and terminator sequences for the tobacco acetolactate synthase gene; 35S=the promoter region from the cauliflower mosaic virus 35S gene; CHS=the promoter region from the snapdragon chalcone synthase gene; Hf1= the DNA sequence encoding petunia flavonoid 3',5'-hydroxylase; D8=terminator sequence from a petunia phospholipid transferase; MAC=the mannopine synthase promoter enhanced with cauliflower mosaic virus 35S gene sequences; DFR=the DNA sequence encoding dihydroflavonol-4-reductase; mas=the terminator sequence from the *Agrobacterium tumefaciens* mannopine synthase gene. Selected restriction enzyme sites are indicated.

FIG. 5 is an autoradiographic representation of a Southern hybridization of DNA isolated from leaf tissue from White Unesco, which had been transformed with a genetic construct (pCGP1470) containing the tobacco acetolactate synthase gene as selectable marker, and the nucleic acid molecule encoding F3',5'H and DFR. Carnation genomic DNA was digested with the restriction endonuclease XbaI and the Southern blot was probed with a $^{32}$P-labelled 730 base-pair fragment of the petunia F3',5'H coding region. Filters were washed in 0.2×SSC/1% w/v SDS at 65° C. Lanes 1–12 represent DNA samples isolated from independent transgenic plants whilst lane 13 is non-transformed White Unesco (negative control). No bands were detected in the non-transformed negative control. Lane 14 represents 33 pg of pCGP1470 plasmid DNA digested with XbaI.

Original colour plates are available for inspection from the Applicant.

DETAILED DESCRIPTION OF THE INVENTION

EXAMPLE 1

Strategy for Altering Flower Colour Using DFR Mutant Cultivars

The flowers of some plants such as, for example, rose, carnation and gerbera, produce two types of anthocyanidins, depending on their genotype—pelargonidin and cyanidin. In the absence of F3'H activity, pelargonidin is produced; in its presence, cyanidin is produced. Pelargonidin is usually accompanied by kaempferol, a colourless flavonol. Cyanidin pigments are usually accompanied by either quercetin or both kaempferol and quercetin. Both pelargonidin and kaempferol are derived from DHK; both cyanidin and quercetin are derived from DHQ (FIG. 1). A number of enzymes, including DFR, ANS and 3GT are required for the conversion of dihydroflavonols (DHK, DHQ and DHM) to the coloured anthocyanins. A third type of anthocyanidin, delphinidin, cannot be produced in flowers of these plants, owing to the natural absence of F3',5'H activity.

In carnation, the DFR enzyme is capable of metabolising two dihydroflavonols, DHK and DHQ, to leucoanthocyanidins which are ultimately converted to anthocyanidin pigments which are responsible for flower colour. DHK is converted to leucopelargonidin giving rise to red-coloured carnations and DHQ to leucocyanidin producing crimson carnations (Geissman and Mehlquist, 1947; Stich et al., 1992b) (see FIG. 1). Carnation DFR is also capable of converting DHM to leucodelphinidin (Forkmann et al., 1987). However, naturally-occurring carnation lines do not contain a flavonoid 3',5'-hydroxylase enzyme and therefore do not synthesise DHM.

The petunia enzyme has a different specificity to that of the carnation DFR. It is able to convert DHQ through no leucocyanidin, but it is not able to convert DHK to leucopelargonidin (Forkmann et al., 1987). In petunia lines containing the F3',5'H enzyme, the petunia DFR enzyme can convert eh DHM produced by the action of F3',5'H to leucodelphinidin, which is further modified giving rise to delphinidin—the pigment responsible for blue-coloured flowers (see FIG. 1). Even though the petunia DFR is capable of converting both DHQ and DHM, it is able to convert DHM far more efficiently, favouring the production of delphinidin (Forkmann et al., 1987).

Carnation is transformable with a nucleic acid molecule encoding the petunia F3',5'H from another species, thereby allowing the production of DHM and ultimately the accumulation of delphinidin (International Patent Application No. PCT/AU94/00265; [WO94/28140]). However, the efficiency of delphinidin product in many of these plants is low due to the competition of carnation DFR with the F3',5'H enzyme for DHK or DHQ as substrate. The accumulation of significant amounts of delphinidin may, therefore, be limited by the action of the carnation DFR.

The inventors have shown that the efficiency of delphinidin product is markedly increased by transformation of a DFR mutant cultivar with an appropriate genetic construct. In such a line there is no accumulation of anthocyanin, due to the absence of DFR enzyme activity. However, when a nucleic acid molecule encoding the petunia DFR enzyme is used to transform this line, together with a nucleic acid molecule encoding flavonoid 3',5'-hydroxylase and both enzymes are expressed, DHK is then converted to leucodelphinidin by the introduced enzymes and ultimately to delphinidic pigments by the plant's endogenous enzymes. If the DFR mutant line is also a F3'H mutant, there is little or no production of DHQ and therefore the only anthocyanins produced by the transgenic plants are delphinidin derivatives. In the presence of the F3'H, cyanidin pigments may also be produced, but delphinidin is the major anthocyanin produced because the petunia DFR is more efficient at utilizing DHM than DHQ as a substrate. Flowers from carnation plants genetically manipulated in this manner produce a range of flower colours covering lilac, violet, purple and blue or various shades thereof. Exemplification of the application of this strategy in accordance with the present invention in the production of carnations with altered flower colour is provided by the following examples.

EXAMPLE 2

Screening of *Dianthus caryophyllus* (carnation) Cultivars a. Flavonol analysis of carnation flowers To identify carnation cultivars having genotypes suitable for application of the strategy of Example 1, white-flowered cultivars were obtained. Flavonols were extracted from each and analysed by thin layer chromatography (TLC), as described in Example 16a. The only flavonol detected in all of these cultivars was kaempferol, indicating that F3'H activity was absent, or substantially reduced, in the flowers of all cultivars.

b. Northern analysis of white carnation cultivars

Northern analysis was then performed, as described in Example 14. After the RNA was transferred from the gel to a Hybond-N filter (Amersham), the filter was probed with the 290 bp BamHI/HindIII cDNA fragment of ANS (described in Example 6) labelled with $^{32}$P. The 1.2 kbp Asp718/BamHI partial DFR clone (described in Example 7) was also labelled with $^{32}$P and used to probe duplicate filters. Prehybridisation (1 hour at 42° C.) and hybridization (16 hours at 42° C.) were carried out as described in Example 14. Filters were washed in 2×SSC, 1% w/v SDS at 65° C. for 1 to 2 hours and then 0.2×SSC, 1% w/v SDS at 65° C. for 0.5 to 1 hours. The Northerns were autoradiographed overnight at −70° C.

Figure 2:
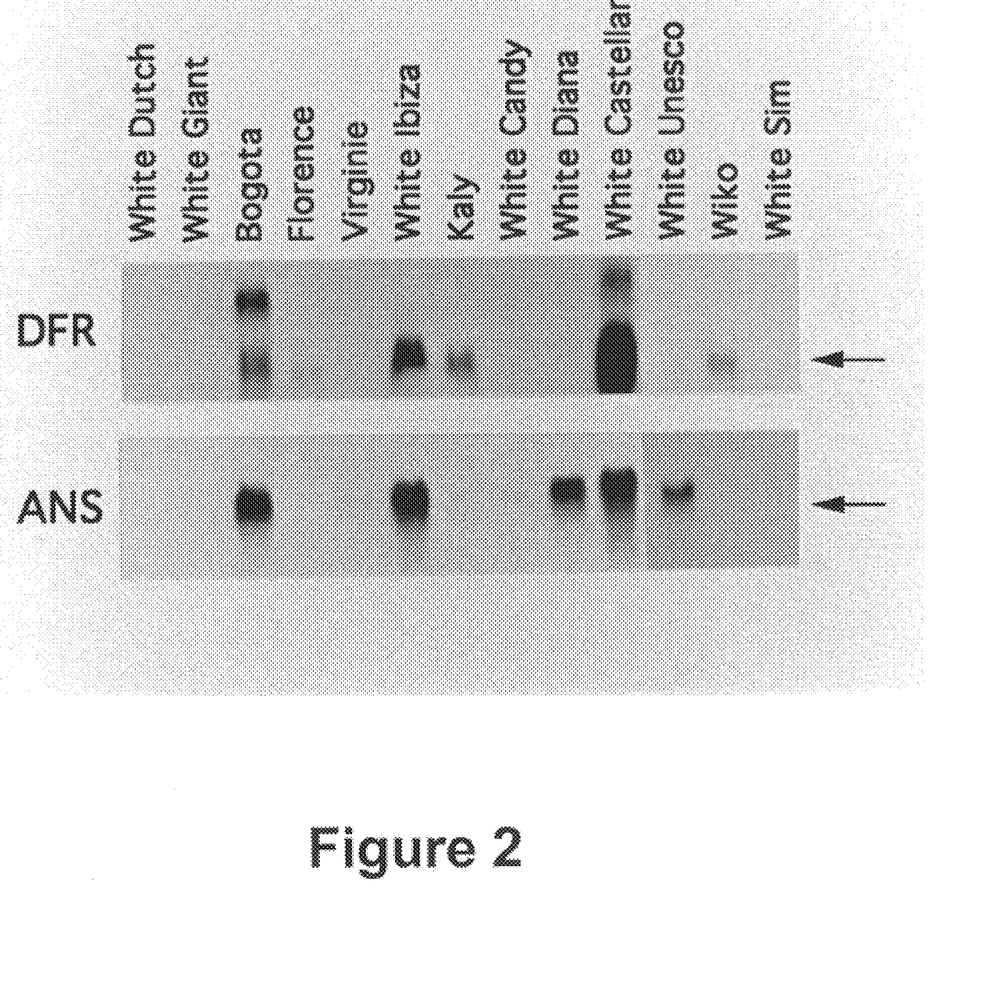
FIG. 2 is an autoradiographic representation of a Northern analysis comparing the expression levels of DFR and ANS mRNA in thirteen commercially-available white carnation cultivars. Arrows point to the relevant transcripts.

This analysis indicated that two of the tested carnation cultivars had no DFR message, while still producing significant levels of ANS mRNA (see FIG. 2). These two carnation cultivars, White Unesco and White Diana, thus appeared to be of the correct genotype for application of this strategy.

c. Leucoanthocyanidin feeding experiments

To confirm that White Diana and White Unesco were not mutated in any of the genes necessary for conversion of leucoanthocyanidin to anthocyanin, precursor feeding experiments were carried out. Petal segments of White Unesco and White Diana were placed in 1 mg/mL solutions of leucopelargonidin and leucocyanidin and incubated for 16 hours at room temperature. Anthocycanin synthesis occurred near the cut edges of the petals in each case. Leucopelargonidin feeding led to the synthesis of pelargonidin, and leucocyanidin led to the synthesis of cyanidin. Anthocyanidin identity was determined by TLC analysis (see Example 16b). Either of these two cultivars was thereby shown to be a suitable candidate for genetic manipulation utilizing the DFR mutant strategy. Further exemplification is provided with cv. White Unesco.

EXAMPLE 3

Biological Reagents

All restriction enzymes and other reagents were obtained from commercial sources and used generally according to the manufacturer's recommendations.

The cloning vector pBluescript II (KS$^+$) was obtained from Stratagene. The SmaI-cut pUC18 cloning vector was obtained from Pharmacia.

EXAMPLE 4

Bacterial Strains

The bacterial strains used in the following examples were:

*Escherichia coli:*

XL1-Blue supE44, hsdR17($r_k$−, $m_k$+), recA1, endA1, byra96(Nal$^r$), thi-1, relA1, lac-, [F'proAB, lacI$^q$, lacZΔM15, Tn10(tet$^r$)] (Bullock et al., 1987).

DH5α supE44, Δ(lacZYA-ArgF), U169, ø80lacZΔM15, hsdR17 ($r_k$−, $m_k$+), recA1, endA1, gyrA96(Nal$^r$), thi-1, relA1, deoR (Hanahan, 1983; BRL, 1986).

*Agrobacterium tumefaciens:*

AGL0 Lazo et al. (1991)

EXAMPLE 5

Plant Growth Conditions

Unless otherwise stated, plants were grown in specialised growth rooms with a 14 hour day length at a light intensity of 10,000 lux minimum and a temperature of 22° C. to 26° C.

EXAMPLE 6

Isolation of a Carnation Anthocyanidin Synthase cDNA Clone a. Polymerase Chain Reaction Primers A Polymerase Chain Reaction (PCR) method was employed to isolate a DNA fragment representing carnation anthocyanidin synthase (ANS). Degenerate oligonucleotides were designed to conserved regions of 2-oxoglutarate-dependent dioxygenase sequences from plants. Oligonucleotides were synthesized on an Applied Biosystems PCR-Mate DNA synthesiser using phosphoramidite chemistry. The oligonucleotides synthesized were:

```
                                              SEQ ID NO:1
   5' AC(A,G)TC(A,G)GT(A,G)TGIGC(T,C)TCIACICC 3'

SEQ ID NO:2
   5' TGGGA(A,G)GA(T,C)TA(T,C)ITITT(T,C)CA 3'
``` b. Isolation of an ANS Fragment from Carnation Petals

Total RNA was extracted from petals of carnation cv. Laguna flowers at stage 1(Stich et al., 1992a) using the method of Turpen and Griffith (1986). Oligo dT (12–18)-primed cDNA was synthesized from 50 µg of total RNA by Superscript™ (BRL) according to the manufacturer's instructions. The cDNA was purified by S200 spun-column chromatography (Pharmacia) followed by ethanol precipitation. PCR amplification was carried out on 50 ng of cDNA in the presence of 10 mM Tris-HCl (pH 8.3), 50 mM KCl, 2 mM MgCl$_2$, 0.01% gelatine, 0.2 mM dATP, 0.2 mM dCTP, 0.2 mM dGTP, 0.2 mM dTTP, 0.4 µM each primer and 1.25 units Taq polymerase (Cetus). The reaction mix (50 µL) was cycled once at each of 95° C. for 3 min; 48° C. for 1 min; 72° C. for 1 min; and then 39 times at each of 95° C. for 1 min; 48° C. for 1 min; 72° C. for 1 min. A DNA fragment of 290 base pairs (bp) was produced.

c. Sequence analysis of carnation ANS fragment

The 290 bp fragment was isolated by Sea Plaque™ low gelling temperature agarose (FMC) electrophoresis in a TAE running buffer (40 mM Tris, 50 mM acetic acid, 50 mM EDTA). The DNA was extracted from the agarose by heating to 65° C., phenol extraction and ethanol precipitation. The fragment was then ligated into a ddT-tailed vector prepared as described by Holton and Graham (1991). Sequencing of plasmid clones was performed using Prism™ Ready Reaction Dye Primer chemistry and a DNA Sequencing System 373A (Applied Biosystems). When compared with the petunia ANS cDNA (Weiss et al., 1993) using FASTA (Pearson and Lipman, 1988) the carnation sequence showed 83% homology at the amino acid level. This 290 bp cDNA fragment was used in Northern analysis of a range of white carnation cultivars (as described in Example 2b).

EXAMPLE 7

Isolation of a Carnation Dihydroflavonol-4-reductase (DFR) cDNA Clone a. Construction of a cDNA library Total RNA was extracted from carnation cv. Laguna petals at stage 9 (Stich et al., 1992a). Polyadenylated RNA was selected using the Oligotex (Qiagen) purification system according to the manufacturer's instruction. A directional cDNA library was constructed using 2 μg of poly(A)$^+$RNA, as a template for cDNA synthesis, and Superscript™ (BRL) according to the manufacturer's instructions. DNA Polymerase I (Klenow fragment) was used to synthesize second strand cDNA which was blunted and ligated to EcoRI adapters. After digestion with XhoI, the cDNA was size-fractionated on a S200 column (Pharmacia). One third of the cDNA was ligated with 1 μg of Uni-Zap™ XR vector (Stratagene). Ligation was carried out at 4° C. for 4 days and then packaged using Packagene™ (Promega). The resultant library contained $1.5 \times 10^5$ plaque forming units (p.f.u.) and was amplified by eluting the bacteriophage from the agar plates into phage storage buffer (100 mM NaCl, 10 mM $MgCl_2$, 10 mM Tris-HCl (pH 7.4), 0.05% w/v gelatine).

b. Screening of the cDNA library

Approximately 100,000 p.f.u. were plated (at 10,000 pfu/plate) onto NZY plates and incubated at 37° C. for 8 hours and then at 4° C. for 1 hour. Thereafter, duplicate colony lifts were taken onto Colony/Plaque Screen™ filters (DuPont) and treated as recommended by the manufacturer. Prior to hybridization, the duplicate filters were prewashed in a solution of 50 mM Tris-HCl pH 8.0, 1 M NaCl, 1 mM EDTA, 0.1% w/v sarcosine (prewashing solution) at 42° C. for 30 minutes followed by similar washes in 0.4 M NaOH and in neutralising solution (0.5 M Tris-HCl pH 8.0, 1.5 M NaCl). After rinsing in 2×SSC, the colony lifts were prehybridized (42° C., 1 hour) and hybridized (42° C., overnight) in a solution of 6×SSC (0.6 M NaCl, 0.06 M sodium citrate), 0.5% w/v sodium dodecyl sulphate (SDS), 0.1% polyvinylpyrrolidone (PVP), 0.1% w/v bovine serum albumin (BSA), 0.1% ficoll, 0.01 M ethylenediaminetetra-acetic acid (EDTA), and 100 mg/mL denatured herring sperm DNA. The full-length $^{32}$P-labelled petunia dihyroflavonol 4-reductase (DFR) cDNA clone from pCGP1403 (Example 8) was used for hybridization. Filters were washed at 65° C. in 2×SSC/1% w/v SDS and exposed to Kodak XAR film with an intensifying screen at −70° C. for 16 hours.

c. Sequence analysis of the carnation DFR cDNA clone

The clones isolated were sequenced using Prism™ Ready Reaction Dye Primer chemistry and a DNA Sequencing System 373A (Applied Biosystems). One clone was found to have homology with the petunia DFR. This clone contained a 1.2 kilobase pair (kbp) cDNA insert and appeared to be a partial DFR clone only.

Double-stranded DNA sequence of the entire cDNA insert was obtained using a shotgun clone sequencing strategy. The DFR cDNA fragment was purified, self-ligated and sheared by ultrasound (four times seven-second bursts at 20 watts from a Branson sonicator with a microprobe attached). The fragment ends were prepared using T4 DNA polymerase and size fractionated in the range of 350 to 600 bp using agarose gel electrophoresis in TAE running buffer. Fragments were purified using Geneclean (Bio101), ligated into SmaI-cut pUC18 and individual clones were sequenced. Comparison of the carnation sequence with the Swissprot protein database using the FASTA program (Pearson and Lipman, 1988) showed that there was 66.9% identity at the amino acid level with the petunia DFR cDNA and 65.7% with the snapdragon DFR. This 1.2 kbp partial DFR clone was used in Northern analysis of a range of white carnation cultivars (as described in Example 2b).

EXAMPLE 8

Isolation of Petunia DFR Genetic Sequences a. Isolation of a functional DFR cDNA clone To isolate a full-length petunia DFR cDNA, 200,000 clones of a *Petunia hybrida* cv. Old Glory Blue λZAP cDNA library (Holton et al., 1993) were screened using a $^{32}$P-labelled 1 kb fragment of a petunia DFR cDNA clone described previously (Brugliera et al., 1994). Twenty clones hybridized strongly with this probe. These clones were picked and plasmids were excised in vitro. DNA sequence analysis revealed that eight of these clones contained the entire protein coding region of DFR, when compared with published sequences (Beld et al., 1989; Huits et al., 1994).

One of the eight full-length petunia DFR cDNA clones, contained in plasmid pCGP1403, was used to screen a carnation cDNA library, as described in Example 7. This full-length clone was further subcloned into a plant expression vector to test for function, as follows. A 1.5 kb Asp718/BamHI fragment of pCGP1403, which contained the DFR cDNA, was ligated with an Asp718/BamHI digest of the vector pCGP40 (International Patent Application No. PCT/AU92/00334 [WO 93/01290]. The resulting plasmid (pCGP1406) contained the petunia DFR cDNA between the MAC promoter (Comai et al, 1990) and the mannopine synthase (mas) terminator (Comai et al, 1990). A BglII digest of this plasmid was used in the construction of pCGP1470, as described in Example 9.

The cDNA clone in plasmid pCGP1406 was shown to be functional by bombardment of *Petunia hybrida* cv. Br140 petals. Br140 lacks DFr activity due to a mutation at the an6 genetic locus, so the flowers are white and do not produce anthocyanins. However, after bombardment of petals with pCGP1406, coloured cells were produced due to anthocyanin synthesis, indicating that the DFR gene fragment present in this plasmid was functional.

b. Isolation of a functional DFR genomic clone

A genomic library was made from *Petunia hybrida* cv. Old Glory Blue DNA in the vector λ2001 (Holton, 1992). Approximately 200,000 p.f.u. were plated out on NZY plates, lifts were taken onto NEN filters and the filters were hybridised with 400,000 cpm/mL of the $^{32}$P-labelled 1 kb petunia DFR cDNA fragment (see 8a, above). Hybridising clones were purified, DNA was isolated from each and mapped by restriction enzyme digestion. A 13 kb SacI fragment of one of these clones was isolated and ligated with SacI-cut pBluescriptII to create pCGP1472. The genomic clone in plasmid pCGP1472 was also shown to be functional by bombardment of *Petunia hybrida* cv. Br140 petals. After bombardment of petals with pCGP1472, coloured cells were produced, due to anthiocyanin synthesis. Finer mapping indicated that a 5 kb BglII fragment contained in the entire DFR gene. This 5 kb fragment was used in the construction of pCGP1473, as described in Example 10.

EXAMPLE 9

Construction of pCGP1470

Plasmid pCGP485 (International Patent Application PCT/AU94/00265 [WO94/28140] was digested with PstI to release a 3.5 kb genetic construct consisting of a snapdragon CHS promoter sequence, a petunia Hf1 cDNA fragment and a petunia phospholipid transfer protein terminator sequence (International Patent Application PCT/AU92/00334 [WO/93/01290). The overhanging 3'-ends of the fragment were removed with T4 DNA polymerase according to standard protocols (Sambrook et al., 1989) before ligation into the SmaI site of the binary vector pWTT2132 (DNAP). The resultant clone was designated pCGP1452.

Figure 3:
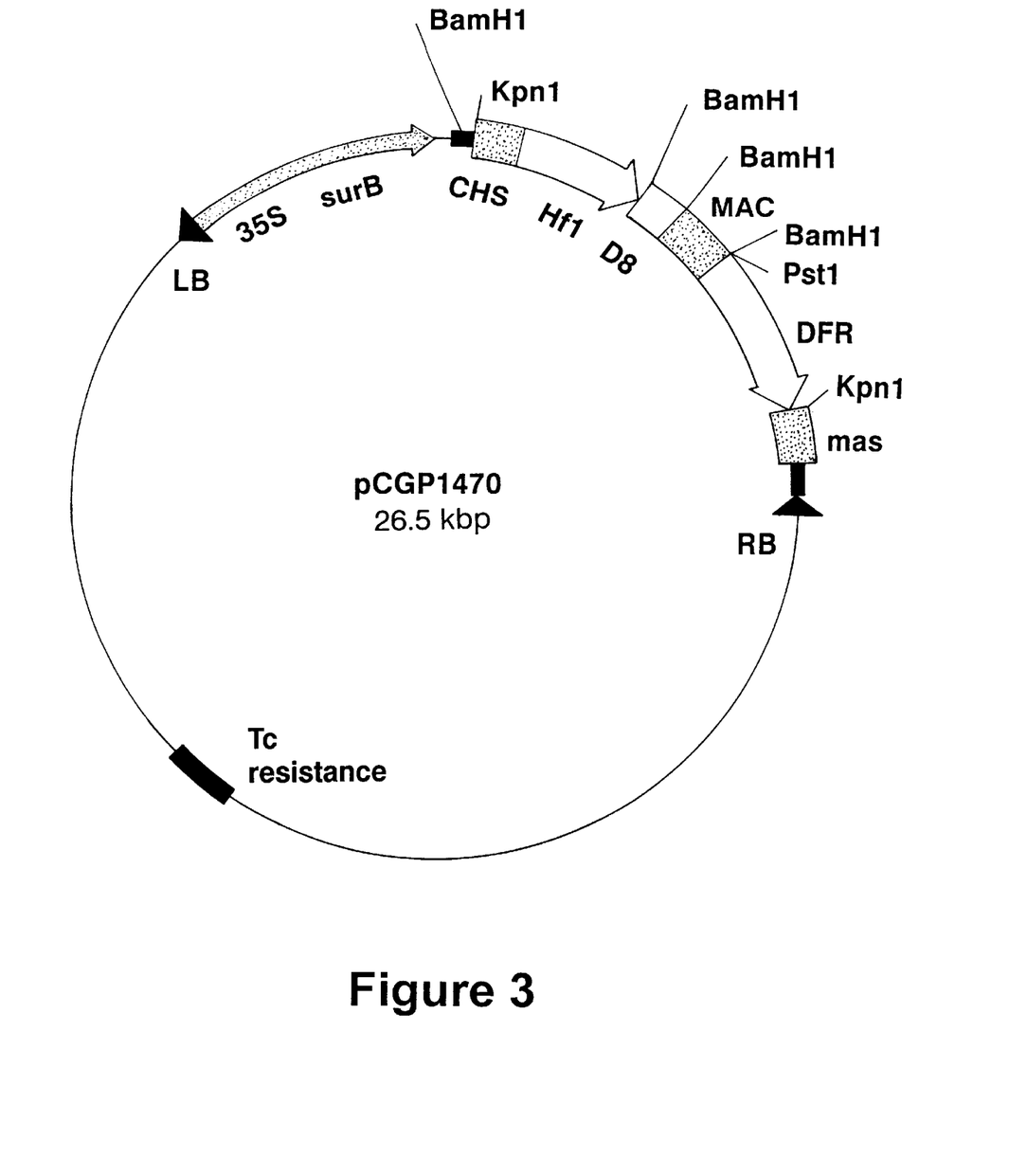

A 3.4 kb genetic construct containing the MAC promoter (Comai et al., 1990), a petunia DFR cDNA (Example 15) and the mannopine synthase (mas) terminator (Comai et al., 1990), was isolated from pCGP1406 as a BglII fragment (see Example 8a). The resulting 5'-overhang was "filled in" using DNA Polymerase I (Klenow fragment) according to standard protocols (Sambrook et al., 1989). The fragment was then ligated into PstI restricted, T4 DNA polymerase-treated pCGP1452 to create pCGP1470. A map of pCGP1470 is presented in FIG. 3.

EXAMPLE 10

Construction of pCGP1473

Figure 4:
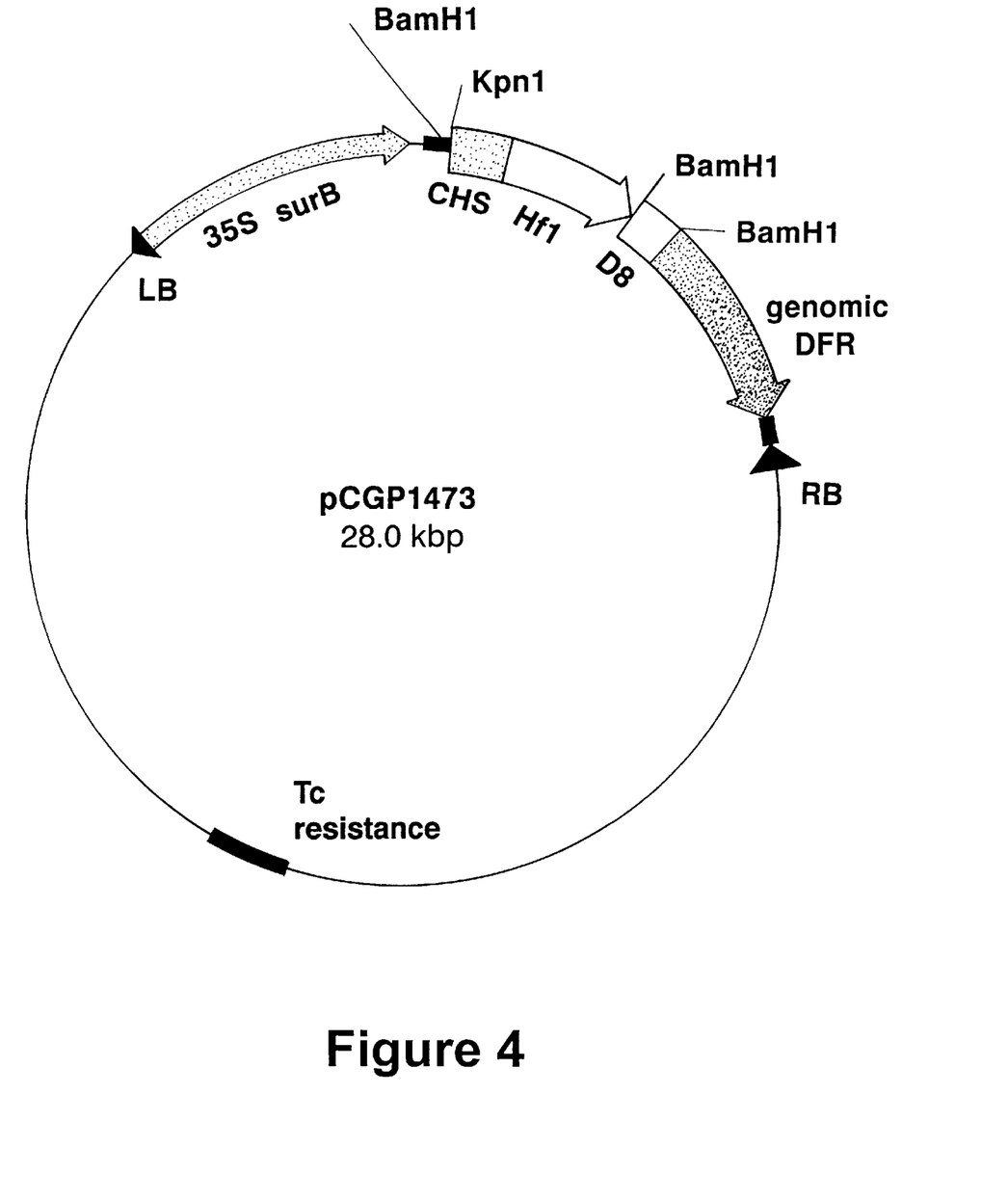
FIG. 4 is a diagrammatic representation of the binary expression vector PCGP1473, construction of which is described in Example 10. Tc resistance=the tetracycline resistance gene; LB=left border; RB=right border; surB=the coding region and terminator sequences for the tobacco acetolactate synthase gene; 35S=the promoter region from the cauliflower mosaic virus 35S gene; CHS=the promoter region from the snapdragon chalcone synthase gene; Hf1= the DNA sequence encoding petunia flavonoid 3',5'-hydroxylase; D8=terminator sequence from a petunia phospholipid transferase; genomic DFR=the DNA sequence encoding dihydroflavonol-4-reductase. Selected restriction enzyme sites are indicated.

A 5 kb BGl II fragment from a petunia DFR genomic clone, pCGP1472 (described in Example 8b), was isolated and the resulting 5'-overhand was "filled in" using DNA Polymerase I (Klenow fragment). The fragment was ligated into the PstI-restricted. T4 DNA polymerase-treated pCGP1452 to create pCGP1473. A map of pCGP1473 is presented in FIG. 4.

EXAMPLE 11

Transformation of *E. Coli* and *A. tumefaciens*

*Escherichia coli* strains DH5α and XL1-Blue, used for routine manipulations, were transformed using the method of Inoue et al. (1990).

The plasmids pCGP1470 and pCGP1473 were introduced into *Agrobacterium tumefaciens* strain AGL0 by adding 5 μg of plasmid DNA to 100 μL of competent *Agrobacterium tumefaciens* cells prepared by inoculating a 50 mL MG/L (Garfinkel and Nester 1980) culture and growing for 16 hours with shaking at 28° C. The cells were then pelleted and resuspended in 1 mL of 20 mM $CaCl_2$. The DNA-Agrobacterium mixture was frozen by incubation in liquid nitrogen for 2 min and then allowed to thaw by incubation at 37° C. for 5 min. The cells were then mixed with 1 mL of MG/L media and incubated with shaking for 4 hours at 28° C. Cells of *A. tumefaciens* carrying pCGP1470 or pCGP1473 were selected on MG/L agar plates containing 50 μg/mL tetracycline. The presence of the plasmid was confirmed by Southern analysis of DNA isolated from the tetracycline-resistant transformants.

EXAMPLE 12

Transformation of *Dianthus caryophyllus* (carnation) cv. White Unesco with nucleic acid molecules encoding DFR and F3'5'H a. Plant Material Carnation cv. White Unesco cuttings were obtained from Van Wyk and Son Flower Supply, Victoria, Australia. The outer leaves were removed and the cuttings were sterilised briefly in 70% v/v ethanol followed by 1.25% w/v sodium hypochlorite (with Tween 20) for 6 min and rinsed three times with sterile water. All the visible leaves and axillary buds were removed under the dissecting microscope before co-cultivation.

b. Co-cultivation of Agrobacterium and Carnation Tissue

*Agrobacterium tumefaciens* strain AGL0 (Lazo et al., 1991), containing the binary vector pCGP1470 or pCGP1473, was maintained at 4° C. on LB agar plates with 50 mg/L tetracycline. A single colony was grown overnight in liquid LB broth containing 50 mg/L tetracycline and diluted to $5 \times 10^8$ cells/mL next day before inoculation. Carnation stem tissue was co-cultivated with Agrobacterium for 5 days on MS medium supplemented with 3% w/v sucrose, 0.5 mg/L benzlaminopurine, 0.5 mg/L 2,4-dichlorophenoxy-acetic acid (2,4-D), 100 μM acetosyringone and 0.25% w/v Gelrite (pH 5.7).

c. Recovery of Transgenic Carnation Plants

For selection of transformed stem tissue, the top 6–8 mm of each co-cultivated stem was cut into 3–4 mm segments, which were then transferred to MS medium (Murashige and Skoog, 1962) supplemented with 0.3% w/v sucrose, 0.5 mg/L BAP, 0.5 mg/L 2,4-D, 1 μg/L chlorsulfuron, 500 mg/L ticarcillin and 0.25% w/v Gelrite. After two-three weeks, explants were transferred to fresh MS medium containing 0.3% sucrose, 0.16 mg/L thidiazuron (TDZ), 0.5 mg/L indole-3-butyric acid (IBA), 2 μg/L chlorsulfuron, 500 mg/L ticarcillin and 0.25% w/v Gelrite and care was taken at this stage to remove axillary shoots from stem explants. After 3 weeks, healthy adventitious shoots were transferred to hormone free MS medium containing 3% w/v sucrose, 3 μg/L chlorsulfuron, 500 mg/L ticarcillin, 0.25% w/v Gelrite. Shoots which survived 3 μg/L chlorsulfuron were transferred to MS medium supplemented with 3% w/v sucrose, 500 mg/L ticarcillin, 5 μg/L chlorsulfuron and 0.25% w/v Gelrite for shoot elongation.

After 2–3 weeks, leaves were pulled from the shoots which had survived selection and were placed on a regeneration medium consisting of MS medium supplemented with 0.22 mg/L TDZ, 0.5 mg/L IBA, 3 μg/L chlorsulfuron, 500 mg/L ticarcillin and 0.25% w/v Gelrite, to obtain shoot regeneration in the presence of selection. Regenerated shoots were transferred to hormone-free MS medium containing 5 μg/L chlorsulfuron, 500 mg/L ticarcillin and 0.25% w/v Gelrite for 2–4 weeks, then to hormone-free MS medium containing 200 mg/L ticarcillin and 0.4% w/v Gelrite, in glass jars, for normalisation. Suncaps (Sigma) were placed on top of the glass jars to hasten the normalisation of shoots. All cultures were maintained under a 16 hour photoperiod (120 μE/m²/s cool white fluorescent light) at 23° C.±2° C. Normalised shoots, approximately 1.5–2.0 cm tall, were rooted on 3 g/kg IBA rooting powder and acclimatised under mist. A soil mix containing 75% perlite/25% peat was used for acclimation, which was carried out at 23° C. under a 14 hour photoperiod (200 μE/m²/s mercury halide light) and typically lasted 3–4 weeks. Plants were fertilised with a carnation mix containing 1 g/L $CaNO_3$ and 0.75 g/L of a mixture of microelements plus N:P:K in the ratio 4.7:3.5:29.2.

EXAMPLE 13

Southern Analysis a. Isolation of Genomic DNA from Carnation

DNA was isolated from 0.3–0.5 grams of leaf tissue using the method of Lassner et al. (1989).

b. Southern Blots

Approximately 1 μg of genomic DNA was digested with XbaI and electrophoresed through a 1% w/v agarose gel in a running buffer of TAE. The DNA was then denatured in denaturing solution (1.5 M NaCl/0.5 M NaOH) for 0.5 to 1.0 hour, neutralised in 0.5 M Tris-HCl (pH 7.5)/1.5 M NaCl for 0.5 to 1.0 hour and the DNA was then transferred to a Hybond-N (Amersham) filter in 20×SSC.

Filters were hybridized with $^{32}$P-labelled DNA ($10^8$ cpm/μg, $2 \times 10^6$ cpm/mL) from a 730 bp EcoRV fragment of a petunia Hf1 cDNA clone. Filters were washed in 2×SSC/1% w/v SDS at 65° C. for 1 hour and then 0.2×SSC/1% w/v SDS at 65° C. for 1 hour.

Figure 5:
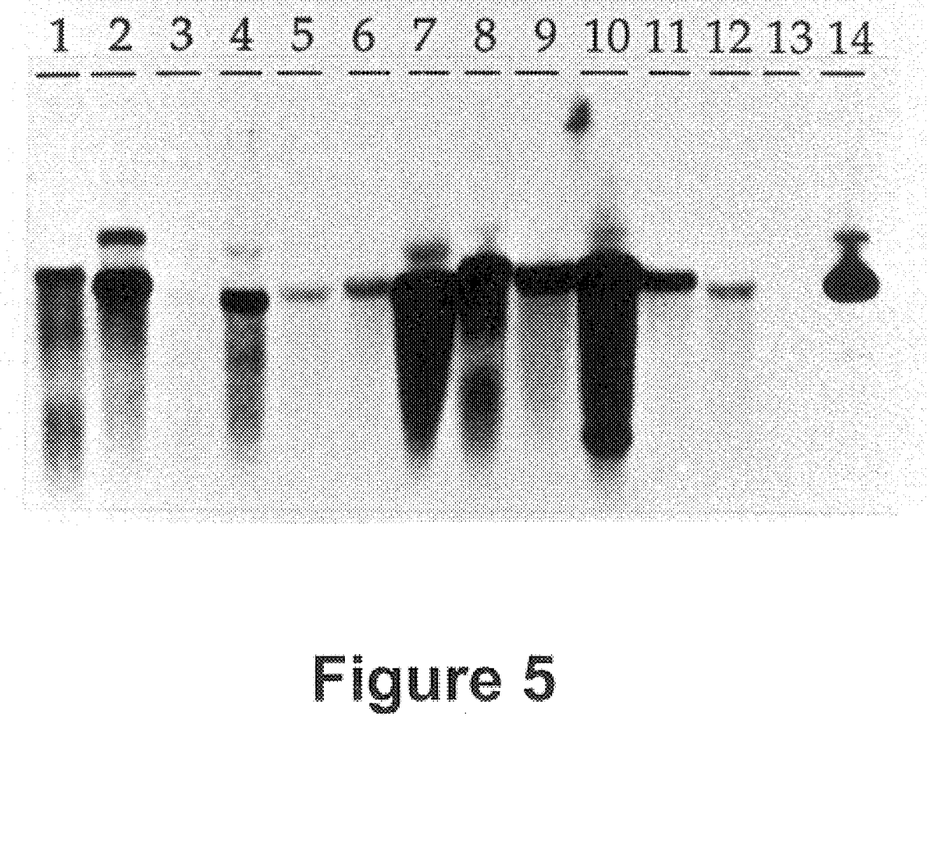
Figure 6A:
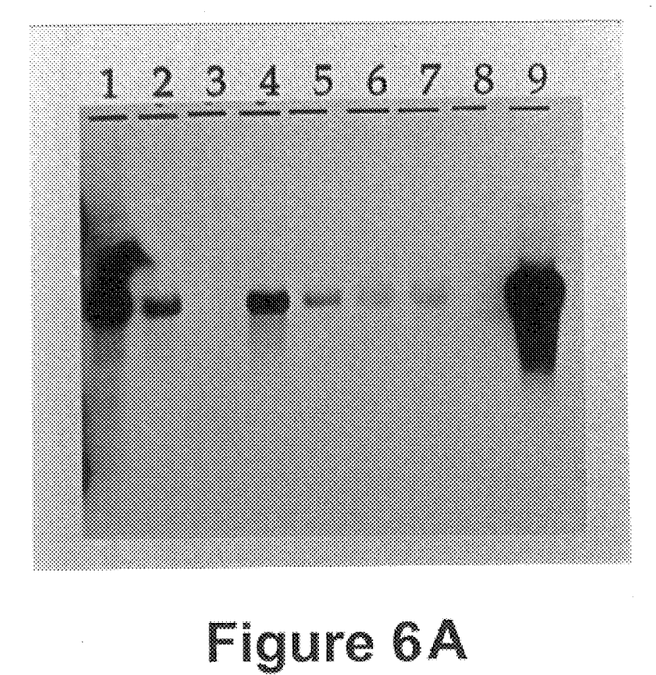
FIGS. 6A–6B are autoradiographic representations of Northern blots of F3',5'H and DFR RNA in petals. Total RNA(10 µg/lane) was analysed from petals of White Unesco plants transformed with pCGP1470 (lanes 1–7), and petals of non-transgenic White Unesco flowers (lane 8). No bands were detected in the non-transformed negative control in lane 8. Lane 9 represents 10 µg of RNA isolated from *Petunia hybrida* cv. Old Glory Blue. A: Northern blot was hybridized with $^{32}$P-labelled DNA from a 730 bp EcoRV fragment of a petunia F3',5'H cDNA clone and washed in 2×SSC/1% w/v SDS at 65° C. for 0.5 hour. B: Northern blot was hybridized with a $^{32}$P-labelled 1.2 kb SacI/XbaI DNA fragment of a petunia DFR cDNA clone from plasmid pCGP1403 (see Example 8a).
Figure 6B:
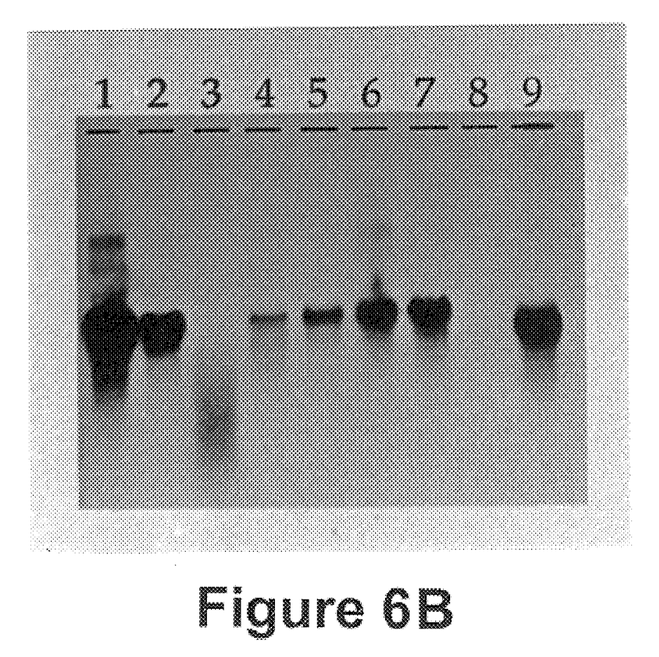
Figure 7:
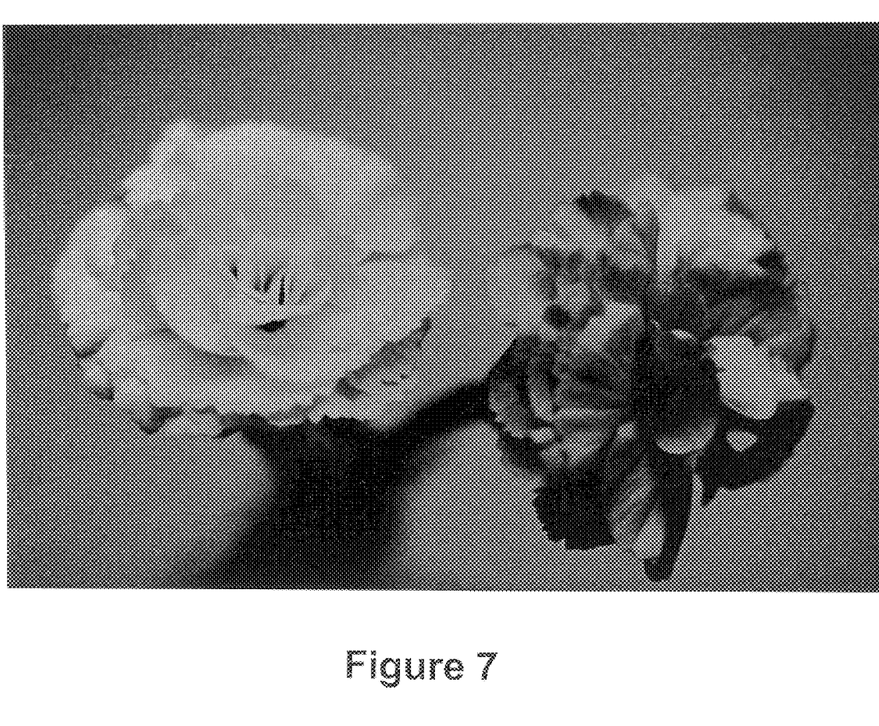
FIG. 7 is a black and white representation of a colour photographic plate representing a non-transgenic control White Unesco flower (the white flower on the left) and a flower from a White Unesco plant transformed with pCGP1470. The transformed plant produces a flower which is lilac/violet in colour.

Southern analysis of putative transgenic carnation plants obtained after selection on chlorsulfuron confirmed the integration of the genetic construct comprising the nucleic acid molecule encoding F3'5'H into the genome, as shown in FIG. 5. Northern analysis of flowers from carnation plants transformed with pCGP1470, performed as described in Example 14, below, confirmed that the introduced nucleic acid molecules defining F3'5'H and DFR were both expressed (see FIG. 6).

EXAMPLE 14

Northern Analysis

Total RNA was isolated from tissue that had been frozen in liquid nitrogen and ground to a fine powder using a mortar and pestle. An extraction buffer of 4 M guanidine isothiocyanate, 50 mM Tris-HCl (pH 8.0), 20 mM EDTA, 0.1% v/v Sarkosyl, was added to the tissue and the mixture was homogenised for 1 minute using a polytron at maximum speed. After the suspension was filtered through Miracloth, it was centrifuged in a JA20 rotor for 10 minutes at 10,000 rpm. The supernatant was transferred to a clean tube and 0.2 grams of CsCl was added for each mL of supernatant. The CsCl was dissolved by mixing and samples were then layered over a 10 mL cusion of 5.7 M CsCl, 50 mM EDTA (pH 7.0) in 38.5 mL Quick-seal centrifuge tubes (Beckman) and centrifuged at 42,000 rpm for 12–16 hours at 23° C. in a Ti-70 rotor. Pellets were resuspended in TE/SDS (10 mM Tris-HCl (pH 7.5), 1 mM EDTA, 1.0% w/v SDS) and extracted with phenol:chloroform (1:1) saturated in 10 mM EDTA (pH 7.5). Following ethanol precipitation the RNA pellets were resuspended in Te/SDS.

RNA samples were electrophoresed through 2.2 M formaldehyde/1.2% w/v agarose gels using running buffer containing 40 mM morpholino-propanesulphonic acid (pH 7.0), 5 mM sodium acetate, 0.1 mM EDTA (pH 8.0). The RNA was transferred to Hybond-N filters (Amersham) as described by the manufacturer and probed with the appropriate $^{32}$P-labelled cDNA fragment ($10^8$ cpm/μg, $2 \times 10^6$ cpm/mL). Prehybridization (1 hour at 42° C.) and hybridization (16 hours at 42° C.) were carried out in 50% v/v formamide, 1 M NaCl, 1% w/v SDS, 10% w/v dextran sulphate. Degraded herring sperm DNA (100 μg/mL) was added with the $^{32}$P-labelled probe for the hybridization step.

Filters were washed in 2×SSC/1% w/v SDS at 65° C. for 1 hour and then 0.2×SSC/1% w/v SDS at 65° C. for 1 hour. All filters were exposed to Kodak XAR film with an intensifying screen at −70° C. for 48 hours.

EXAMPLE 15

Altered flower phenotype

The expression of the introduced nucleic acid molecules representing F3'5'H and DFR in the DFR/F3'H mutant carnation cultivar White Unesco had a marked effect on flower colour. The flowers of the non-transgenic plants are white, whereas the transgenic plants produced flowers which were a lilac/violet colour. The colour changes observed may also be described in terms of numbers from the Royal Horiticultural Society's Colour Chart. In general, the changes can be described as moving the colour from white to the purple/violet/blue hues represented by many, but not all, of the colour squares between 80 and 98.

Although not wishing to limit the possible colour changes which may be achieved, some of the colours observed in flowers of transformed White Unesco plants could be described, approximately, as having changed from white (untransformed) to 84B/C (transformed). Furthermore, the use of a stronger promoter to direct expression of the introduced nucleic acid molecules may allow production of even higher amounts of delphinidin pigment, thereby causing the development of colours of bluer hue. It should be remembered that other biochemical and physiological conditions such as petal pH, extend of co-pigmentation and degree of acylation of anthocyanins will also affect the individual outcome. These can be manipulated by transformation of other suitable cultivars, or by co-transformation with nucleic acid molecules affecting pH co-pigmentation or acylation. This may enable the development of colours of bluer hue. The citing of specific colours achieved should not be interpreted as defining or limiting the possible range.

EXAMPLE 16

Flavonoid analyses a. TLC analysis of flavonols

Approximately 0.5 gram of fresh carnation petal tissue was added to 1 mL of 2 M HCl in a 1.5 mL microcentrifuge tube (Eppendorf) and heated in a boiling water bath for 30 minutes. Cellular debris was pelleted by centrifugation at 14,000 rpm for 5 minutes and 500 μL of supernatant was transferred to a clean microcentrifuge tube. Flavonoids were extracted with 200 μL ethylacetate and centrifuged briefly to separate the phases. The upper (ethylacetate) phase was transferred to a new microcentrifuge tube, dried down under vacuum in a SpeedVac Concentrator (Savant) and resuspended in 15 μL ethylacetate and a 2 μL aliquot was spotted onto a cellulose TLC sheet (20 cm×20 cm, Merck) and run for approximately 3–4 hours in Forestal solvent (30 parts acetic acid: 3 parts HCl: 10 parts water). The TLC plate was then allowed to air dry and the flavonols were viewed under ultraviolet light.

b. TLC analysis of anthocyanidins

Two carnation petals were added to 1 mL of 2 M HCl in a 1.5 mL microcentrifuge tube (Eppendorf) and heated in a boiling water bath for 30 minutes. Cellular debris was pelleted by centrifugation at 14,000 rpm for 5 minutes and 500 μL of supernatant was transferred to a clean microcentrifuge tube. Anthocyanidins were extracted with 200 μL of iso-amylalcohol (IAA) and centrifuged briefly to separate the phases. The upper phase (IAA) was transferred to a new tube, dried down under vacuum and resuspended in 20 μL of IAA and a 1 μL aliquot was spotted onto a cellulose TLC sheet (20×20 cm, Merck) and run for approximately 3–4 hours in Forestal solvent. The TLC plate was allowed to air dry and the anthocyanidins could be viewed under normal light.

c. HPLC analysis of anthocyanidins

Anthocyanins were extracted and hydrolysed by incubating approximately 0.5 g carnation petals with 1 mL of 2 M HCl at 100° C. for 30 minutes. Anthocyanidins were extracted with 200 μL of IAA. One quarter of this mixture was dried down under vacuum and resuspended in 200 μL of 50% acetonitrile and 0.5% TFA (tri-fluoro acetic acid). A 5 μL aliquot was analysed by HPLC via gradient elution using gradient conditions of 50%B to 60%B over 10 minutes, then 60%B for 10 minutes and finally 60%B to 100%B over 5 minutes, where solvent A consisted of TFA::water (5:995) and solvent B consisted of acetonitrile:TFA::water (500:5:495). An Asahi Pac ODP-50 cartridge column (250 mm×4.6 mm, internal diameter) was used for the reversed phase chromatographic separations. The flow rate was 1 mL/minute and the temperature was 40° C. The detection of anthocyanidins was carried out using a Shimadzu SPD-M6A three-dimensional detector at 400–650 nm.

EXAMPLE 17

Bombardment of petals with DNA-coated microprojectiles

Particle bombardment using 1 μm gold particles were performed essentially as described by Sanford et al. (1993). The biolistic Bio-Rad PDS-100 helium-driven gun with 1100 psi rupture disks was used for all bombardments. Petals were dissected from opening carnation flower buds and placed on top of a plate of MS medium (+0.25% gelrite) before bombardment. Each plate was bombarded twice with an independently-prepared batch of DNA-coated gold particles. The plasmid DNA used for bombardment was purified using either a CsCl gradient method (Sambrook et al., 1989) or a Qiagen column (Qiagen). One microgram of DNA was used per shot.

EXAMPLE 18

$^{32}$P-Labelling of DNA Probes

DNA fragments (50 to 100 ng) were radioactively labelled with 50 μCi of [α-$^{32}$P]-dCTP using an oligolabelling kit (Bresatec). Unincorporated [α-$^{32}$P]-dCTP was removed by chromatography on a Sephadex G-50 (Fine) column as described by Sambrook et al. (1989).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

Beld, M., Martin, C., Huits, H., Stuitje, A. R. And Gerats, A. G. M. *Plant Molecular Biology* 13: 491–502, 1989.

Bethesda Research Laboratories. BRL pUC host: *E. coli* DH5α competent cells. *Bethesda Res. Lab. Focus.* 8(2): 9, 1986.

Brugliera, F., Holton, T. A., Stevenson, T. W., Farcy, E., Lu, C-Y. and Cornish, E. C., *The Plant Journal* 5(1): 81–92, 1994.

Bullock, W. O., Fernandez, J. M. and Short, J. M. *BioTechniques* 5:376, 1987.

Comai, L., Moran, P. and Maslyar, D., *Plant Molecular Biology* 15: 373–381, 1990.

Ebel, J. and Hahlbrock, K., In: *The Flavonoids: Advances in Research Since* 1980. Harbourne, J. B. (ed.), Academic Press, New York, USA 641–679, 1988.

Forkmann, G. *Plant Breeding* 106: 1–26, 1991.

Forkmann, G., and Ruhnau, B. *Z. Naturforsch.* 42c: 1146–1148, 1987.

Garfinkel, D. J. and Nester, E. W., *J.Bact.* 144: 732–743, 1980.

Geissman, T. A. and Mehlquist, G. A. L. *Genetics* 32: 410–433, 1947.

Hahlbrock, K. and Grisebach, H., *Annu. Rev. Plant Physiol.* 30: 105–130, 1979.

Hanahan, D. *J. Mol. Biol.* 166: 557, 1983.

Holton, T. A., and Graham, M. W. *Nucleic Acids Research* 19(5): 1156, 1991.

Holton, T. A. Isolation and characterisation of petal-specific genes from *Petunia hybrida*. PhD Thesis, University of Melbourne, 1992.

Holton, T. A., Brugliera, F. and Tanaka, Y. *The Plant Journal* 4(6): 1003–1010, 1993.

Huits, H. S. M., Gerats, A. G. M., Kreike, M. M., Mol, J. N. M. and Koes, R. E. *The Plant Journal* 6(3): 295–310, 1994.

Inoue, H., Nojima, H. and Okayama, H., *Gene* 96: 23–28, 1990.

Lassner *et al. Plant Molecular Biology Reporter* 7: 116–128, 1989.

Lazo, G. R., Pascal, A. S. and Ludwig, R. A. *Bio/technology* 9: 963–967, 1991.

Murashige, T. and Skoog, F. *Physiol. Plant* 15: 73–97, 1962.

Pearson, W. R. and Lipman, D. J. *Proc. Natl. Acad. Sci. (USA)* 85: 2444–2448, 1988.

Sambrook, J., Fritsch, E. F. and Maniatis, T. *Molecular Cloning: A Laboratory Manual* (2nd edition), Cold Spring Harbor Laboratory Press, USA, 1989.

Sanford, J. C., Klein, T. M., Wolf, E. D. and Allen, N. *Journal of Particle Science Technology* 5: 27–37, 1993.

Schram, A. W., Jonsson, L. M. V. and Bennink, G. J. H., Biochemistry of flavonoid synthesis in *Petunia hybrida*. In: *Petunia* Sink, K. C. (ed.), Springer-Verlag, Berlin, Germany, pp 68–75, 1984.

Stafford, H. A., *Flavonoid Metabolism*. CRC Press, Inc. Boca Raton, Fla., USA, 1990.

Stich, K., Eidenberger, T., and Wurst, F. *Z. Naturforsch.* 47c: 553–560, 1992a.

Stich, K., Eidenberger, T., and Wurst, F., and Forkmann, G. *Planta* 187: 103–108, 1992b.

Stoz, G. and Formann, G. *Z. Naturforsch* 37c: 19–23, 1982.

Turpen, T. H. and Griffith, O. M., *BioTechniques* 4: 11–15, 1986.

Weiss, D., van der Luit, A. H., Kroon, J. T. M., Mol, J. N. M. and Kooter, J. M. *Plant Molecular Biology* 22: 893–897, 1993.

Wiering, H. and de Vlaming, P., Inheritance and Biochemistry of Pigments. In: *Petunia* Sink, K. C. (ed.) Springer-Verlag, Berlin, Germany, pp 49–65, 1984.

What is claimed is:

1. A method of producing a transgenic plant exhibiting altered flower colour, said method comprising:
   (1) selecting a first plant which is incapable of synthesizing a DFR which acts on DHK, or produces reduced levels of DFR compared to a wild type plant, or produces a DFR with a reduced substrate specificity for DHK compared to DHQ or DHM; and
   (2) introducing into said first plant one or more genetic constructs comprising a nucleotide sequence encoding a F3'5'H and a nucleotide sequence encoding a DFR which acts on DHM but is either incapable of acting on DHK or has a greater substrate specificity for DHM than for DHK or DHQ, to produce said transgenic plant, wherein said transgenic plant has altered flower colour compared to said first plant.

2. The method according to claim 1 wherein the plant is carnation, rose, gerbera or chrysanthemum.

3. The method according to claim 2 wherein the plant is carnation.

4. The method according to any one of claims 1–3 wherein the first plant also is incapable of synthesizing a F3'H.

5. The method according to claim 1 wherein the nucleotide sequence encoding a DFR is from petunia.

6. The method according to claim 1 wherein the nucleotide sequence encoding a F3'5'H is from petunia, eggplant, lisianthus, gentian, pansy, China aster, anemone, grape, iris, hyacinth, delphinium or bell flower.

7. The method according to claim 6 wherein the nucleotide sequence encoding a F3'5'H is from petunia.

8. The method according to claim 1 wherein the altered flower colour is a hue of lilac, violet, purple, or blue.

9. A transgenic carnation plant produced by:
   (1) selecting a first carnation plant having an inability to synthesize a DFR which acts on DHK, or having reduced levels of DFR compared to a wild type plant, or having a DFR with a reduced substrate specificity for DHK compared to DHQ or DHM; and
   (2) introducing into said first carnation plant a heterologous DFR which acts on DHM but is either incapable of acting on DHK, or has a greater substrate specificity for DHM than for DHK or DHQ, wherein said transgenic carnation plant has an altered flower colour relative to said first carnation plant.

10. The transgenic carnation plant according to claim 9 wherein said first carnation plant also has an inability to synthesize a F3'H.

11. A cut flower or a cut plant part comprising a flower from the transgenic carnation plant of claim 9 or claim 10.

12. A transgenic plant exhibiting altered flower colour produced by:
(1) selecting a first plant which is incapable of synthesizing a DFR which acts on DHK, or which produces reduced levels of DFR compared to a wild type plant, or which produces a DFR with a reduced substrate specificity for DHK compared to DHQ or DHM; and
(2) introducing into said first plant a nucleic acid molecule comprising a nucleotide sequence encoding a F3'5'H and a nucleotide sequence encoding a DFR which acts on DHM but is either incapable of acting on DHK or which has a greater substrate specificity for DHM than for DHK or DHQ, wherein said transgenic plant has an altered flower colour relative to said first plant.

13. The transgenic plant according to claim 12 wherein the plant is carnation, rose, gerbera or chrysanthmum.

14. The transgenic plant according to claim 13 wherein the plant is carnation.

15. The transgenic plant according to any one of claims 12–14 wherein the first plant also is incapable of synthesizing a F3'H.

16. The transgenic plant according to claim 12 wherein the nucleotide sequence encoding a DFR is from petunia.

17. The transgenic plant according to claim 12 wherein the nucleotide sequence encoding a F3'5'H is from eggplant, lisianthus, gentian, pansy, China aster, anemone, grape, iris, hyacinth, delphinium or bell flower.

18. The transgenic plant according to claim 17 wherein the nucleotide sequence encoding a F3'5H is from petunia.

19. The transgenic plant according to claim 12 wherein the altered flower colour is a hue of lilac, violet, purple, or blue.

20. A cut flower from the transgenic plant according to claim 12 or claim 19.

21. A plant tissue or plant organ from the transgenic plant of claim 12 or claim 19.

* * * * *

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Synthesized
<220> FEATURE:
<221> NAME/KEY: modified base
<222> LOCATION: 12
<223> OTHER INFORMATION: n is inosine
<220> FEATURE:
<221> NAME/KEY: modified base
<222> LOCATION: 18
<223> OTHER INFORMATION: n is inosine
<220> FEATURE:
<221> NAME/KEY: modified base
<222> LOCATION: 21
<223> OTHER INFORMATION: n is inosine

<400> SEQUENCE: 1
acrtcrgtrt gngcytcnac ncc                                    23

<210> SEQ ID NO 2
<211> LENGTH: 20
<212> TYPE: DNA
<213> ORGANISM: Artificial Sequence
<220> FEATURE:
<223> OTHER INFORMATION: Synthesized
<220> FEATURE:
<221> NAME/KEY: modified base
<222> LOCATION: 13
<223> OTHER INFORMATION: n is inosine
<220> FEATURE:
<221> NAME/KEY: modified base
<222> LOCATION: 15
<223> OTHER INFORMATION: n is inosine

<400> SEQUENCE: 2
tgggargayt ayntnttyca                                        20